(12) United States Patent
Jeong

(10) Patent No.: US 11,402,142 B2
(45) Date of Patent: Aug. 2, 2022

(54) DEODORIZING APPARATUS COMPRISING SUCTION FAN, AND REFRIGERATOR INCLUDING THE SAME

(71) Applicant: Seoul Viosys Co., Ltd., Ansan-si (KR)

(72) Inventor: Jae Hak Jeong, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 383 days.

(21) Appl. No.: 16/486,579

(22) PCT Filed: Feb. 14, 2018

(86) PCT No.: PCT/KR2018/001946
§ 371 (c)(1),
(2) Date: Aug. 16, 2019

(87) PCT Pub. No.: WO2018/151535
PCT Pub. Date: Aug. 23, 2018

(65) Prior Publication Data
US 2020/0386466 A1    Dec. 10, 2020

(30) Foreign Application Priority Data

Feb. 16, 2017 (KR) ........................ 10-2017-0021256

(51) Int. Cl.
*F25D 17/04* (2006.01)
*F24F 3/16* (2021.01)
(Continued)

(52) U.S. Cl.
CPC .............. *F25D 17/042* (2013.01); *F24F 3/16* (2013.01); *F25D 27/00* (2013.01); *F25D 29/00* (2013.01);
(Continued)

(58) Field of Classification Search
CPC ....... F24F 3/16; F24F 8/22; F24F 8/50; F25D 27/00; F25D 27/005; F25D 29/00;
(Continued)

(56) References Cited

U.S. PATENT DOCUMENTS 9,671,149 B2   6/2017   Kim et al.
9,702,611 B2   7/2017   Kang et al.
(Continued)

FOREIGN PATENT DOCUMENTS

CN   2589913        12/2003
CN   102589241      7/2012
(Continued)

OTHER PUBLICATIONS

International Search Report dated Jun. 12, 2018, in International Application No. PCT/KR2018/001946 (with English Translation).
(Continued)

*Primary Examiner* — Emmanuel E Duke
(74) *Attorney, Agent, or Firm* — H.C. Park & Associates, PLC

(57) ABSTRACT

A deodorizing apparatus including: a base, in which a suction port and a discharge port are disposed; a cover coupled to the base; a suction fan fixed to the base so as to suction air through the suction port; a first fixing member disposed between the suction port and the discharge port so as to support a filter; a light emitting module including a light emitting diode; and a second fixing member for supporting the light emitting module. The first fixing member includes a first body part for spacing the filter apart from the base.

20 Claims, 10 Drawing Sheets

(51) Int. Cl.
  *F25D 27/00* (2006.01)
  *F25D 29/00* (2006.01)
  *F24F 8/22* (2021.01)
(52) U.S. Cl.
  CPC ........ *F24F 8/22* (2021.01); *F25D 2317/0415* (2013.01); *F25D 2317/0417* (2013.01); *F25D 2317/0681* (2013.01)
(58) Field of Classification Search
  CPC ..... F25D 2317/0415; F25D 2317/0417; F25D 2317/0681; F25D 17/04; A61L 2209/111; A61L 2209/14; A61L 9/205
  See application file for complete search history.

(56) References Cited

U.S. PATENT DOCUMENTS

| | | | |
|---|---|---|---|
| 2004/0007000 A1* | 1/2004 | Takeda | F24F 1/0087 62/78 |
| 2007/0227174 A1* | 10/2007 | Kang | B01D 46/50 62/331 |
| 2012/0181911 A1 | 7/2012 | Kim et al. | |
| 2012/0204581 A1* | 8/2012 | Kang | F25D 17/042 62/78 |
| 2015/0033784 A1* | 2/2015 | Park | F25D 11/00 62/264 |
| 2017/0191728 A1* | 7/2017 | Seo | F25D 17/042 |
| 2019/0083674 A1 | 3/2019 | Jeong et al. | |

FOREIGN PATENT DOCUMENTS

| | | | |
|---|---|---|---|
| CN | 106247748 | 12/2016 | |
| EP | 1953481 | 8/2008 | |
| EP | 2144021 | 1/2010 | |
| EP | 2487438 | 8/2012 | |
| JP | 2001-074349 | 3/2001 | |
| KR | 10-2006-0010105 | 2/2006 | |
| KR | 2006-0010105 | 2/2006 | |
| KR | 10-2006-0080025 | 7/2006 | |
| KR | 10-2006-0087894 | 8/2006 | |
| KR | 2006-0087894 | 8/2006 | |
| KR | 10-2012-0082992 | 7/2012 | |
| KR | 10-2014-0124659 | 10/2014 | |
| WO | 2016/089088 | 6/2016 | |
| WO | WO-2016089088 A1 * | 6/2016 | .......... B01D 53/885 |
| WO | 2019/037983 | 2/2019 | |

OTHER PUBLICATIONS

Extended European Search Report dated Nov. 18, 2020, issued in European Patent Application No. 18754838.3.
Extended European Search Report dated Mar. 2, 2021, issued in European Patent Application No. 18754838.3.
Office Action dated Dec. 18, 2020, from the Chinese Patent Office for Chinese Patent Application No. 201880009123.8.

* cited by examiner

DEODORIZING APPARATUS COMPRISING SUCTION FAN, AND REFRIGERATOR INCLUDING THE SAME

CROSS REFERENCE TO RELATED APPLICATION

This application is a National Stage Entry of International Patent Application No. PCT/KR2018/001946, filed on Feb. 14, 2018, and claims priority from and the benefit of Korean Patent Application No. 10-2017-0021256, filed on Feb. 16, 2017, each of which is incorporated by reference for all purposes as if fully set forth herein.

BACKGROUND

Field

Exemplary embodiments of the present invention relate to an electronic apparatus, and more particularly, to a deodorizing device including a suction fan and a refrigerator including the deodorizing device.

Discussion of the Background

Refrigerators are household appliances allowing preserved foods to be kept fresh and stored for a long period of time by freezing or refrigerating the preserved foods therein through repeated circulation of chilled air.

When preserved foods, such as vegetables and fruit, are stored in refrigerators, gases generated from the preserved foods are known as a main factor deteriorating freshness of the preserved foods. For example, ethylene is a gas generated due to aging of some kinds of fruit and acts as a material accelerating aging of vegetables, fruit, and the like, and the generation of ethylene may be sharply increased by a positive feedback process. Therefore, if gases, such as ethylene, generated from preserved foods are not controlled, the preserved foods may not be stored for a long period of time while being kept fresh.

To solve such a problem, a deodorizing device may be provided inside a refrigerator. The deodorizing device may allow air in the refrigerator to be kept fresh by removing several gases. Such a deodorizing device is required to have high deodorizing efficiency with respect to air to be treated while deodorizing a large amount of air per hour. In addition, such a deodorizing device is attached to the interior of the refrigerator and is required to have a relatively small size, for example, a small thickness.

The above information disclosed in this Background section is only for understanding of the background of the inventive concepts, and, therefore, it may contain information that does not constitute prior art.

SUMMARY

Exemplary embodiments of the present invention provide a deodorizing device, which has a reduced size and can deodorize a large amount of air per hour, and a refrigerator including the deodorizing device.

An exemplary embodiment of the present invention provides a deodorizing device including: a base, in which a suction port and a discharge port are disposed; a cover coupled to the base; a suction fan secured to the base and suctioning air through the suction port; a first securing member disposed between the suction port and the discharge port and supporting a filter; a light emitting module including a light emitting diode; and a second securing member supporting the light emitting module. The first securing member includes a first body portion separating the filter from the base.

The first securing member may further include second and third body portions including sliding grooves for receiving the filter, and the first body portion may be disposed between the second and third body portions.

The first to third body portions and a portion of the cover may surround the filter, and the first to third body portions may block the air.

The suction fan may suction the air through the suction port in a first direction and the first securing member may support the filter such that a surface of the filter, through which the air passes, faces in a second direction intersecting the first direction.

The second securing member may be disposed between the suction port and the first securing member.

The second securing member may include: first and second poles including grooves for securing the light emitting module; and a third pole disposed between the first and second poles and having a protrusion for further securing one side of the light emitting module.

The deodorizing device may further include a photosensor sensing intensity of light emitted from the light emitting diode, wherein an alarm signal may be generated when the sensed intensity of light is lower than a threshold value.

The deodorizing device may further include an air sensor sensing air, wherein the suction fan and the light emitting module may be driven according to a sensing result of the air sensor.

Another exemplary embodiment of the present invention provides a deodorizing device including: a base, in which a suction port and first and second discharge ports are disposed; a cover coupled to the base; a suction fan secured to the base and suctioning air through the suction port; a first securing member disposed between the suction port and the first discharge port and supporting a first filter; a first light emitting module including a first light emitting diode; a second securing member supporting the first light emitting module; a third securing member disposed between the suction port and the second discharge port and supporting a second filter; a second light emitting module including a second light emitting diode; and a fourth securing member supporting the second light emitting module. Each of the first and third securing members includes a first body portion separating the corresponding filter from the base.

Each of the first and third securing members may further include second and third body portions including sliding grooves for receiving the corresponding filter, and the first body portion may be disposed between the second and third body portions.

The first to third body portions and the cover may surround the corresponding filter, and the first to third body portions may block the air.

Another exemplary embodiment of the present invention provides a refrigerator including: a main body; a door secured to the main body to open and close the main body; a deodorizing device secured inside the main body; and a main controller controlling the deodorizing device. The deodorizing device includes: a base in which a suction port and a discharge port are disposed; a cover coupled to the base; a suction fan secured to the base and suctioning air through the suction port; a first securing member disposed between the suction port and the discharge port and supporting a filter, the first securing member including a body portion separating the filter from the base; a light emitting module including a light emitting diode; a second securing member supporting the light emitting module; and a controller controlling the suction fan and the light emitting module.

The main controller may enable a control signal when the door is closed, and the controller may operate the suction fan and the light emitting module when the control signal is enabled.

The deodorizing device may include visible light emitting diodes arranged on the base and operating in response to control by the controller, wherein the controller may operate the visible light emitting diodes when the control signal is disabled.

The refrigerator may further include a display device, wherein the deodorizing device may further include a photosensor sensing intensity of light emitted from the light emitting diode, the controller may generate an alarm signal when the sensed intensity of light is lower than a threshold value, and the main controller may display requirement for replacement of the light emitting diode in response to the alarm signal on the display device.

The refrigerator may further include a display device, wherein the deodorizing device may further include an air sensor that senses air passing through the filter, the controller may generate alarm signals according to sensing results of the air sensor, and the main controller may display requirement for replacement of the light emitting diode on the display device based on the alarm signals.

According to exemplary embodiments, a deodorizing device, which has a reduced size and deodorizes a large amount of air per hour, and a refrigerator including the deodorizing device are provided.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide a further understanding of the disclosure and are incorporated in and constitute a part of this specification, illustrate exemplary embodiments of the disclosure, and together with the description serve to explain the inventive concepts.

DETAILED DESCRIPTION

Figure 1:
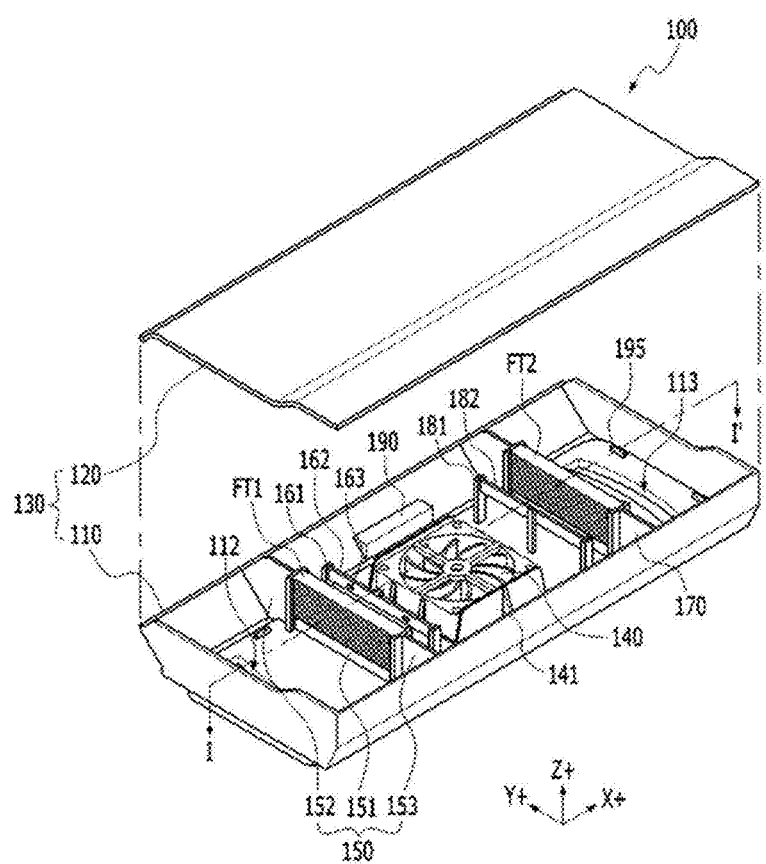
FIG. 1 is an exploded perspective view of a deodorizing device according to an exemplary embodiment of the present invention.

In the following description, for the purposes of explanation, numerous specific details are set forth in order to provide a thorough understanding of various exemplary embodiments of the invention. As used herein "embodiments" are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

FIG. 1 is an exploded perspective view of a deodorizing device 100 according to an exemplary embodiment of the present invention.

Referring to FIG. 1, the deodorizing device 100 includes a housing 130 including a base 110 and a cover 120, a suction fan 140, a first securing member 150, a first filter FT1, a second securing member 161, a first light emitting module 162, a third securing member 170, a second filter FT2, a fourth securing member 181, a second light emitting module 182, and a controller 190.

The base 110 includes a suction port and first and second discharge ports 112, 113. The suction port is disposed between the first and second discharge ports 112, 113. For example, the suction port may be disposed in a central region of the base 110 (see 111 of FIG. 2).

The cover 120 is coupled to the base 110 to define an internal space of the housing 130. In an exemplary embodiment, the cover 120 may contact the first and second filters FT1, FT2 as well as the base 110. The cover 120 may be coupled to the base 110 in various ways. For example, the cover 120 may be configured to be easily coupled to and separated from the base 110.

The suction fan 140 is secured to the base 110 to overlap the suction port. For example, the suction fan 140 may be secured to the base 110 by a securing member 141 having a suitable shape. The suction fan 140 operates in response to control by the controller 190. The suction fan 140 suctions air in a Z+ direction through the suction port in an operation mode. In an exemplary embodiment, an outer periphery of the suction fan 140 may be packed with a material, such as rubber, functioning as a buffer to reduce noise during operation of the suction fan 140.

The first securing member 150 is disposed between the first discharge port 112 and the suction fan 140. The first securing member 150 supports the first filter FT1 such that one surface of the first filter FT1 faces the suction fan 140 in an X+ direction intersecting the Z+ direction.

According to an exemplary embodiment, the first securing member 150 includes first to third body portions 151 to 153. The first body portion 151 is disposed between the second and third body portions 152, 153. The first body portion 151 is disposed between the first filter FT1 and a bottom surface of the base 110 and thus separates the first filter FT1 from the bottom surface of the base 110 by a certain distance. Thus, manufacturing costs of the filter FT1 is reduced while improving deodorizing efficiency of the deodorizing device 100. This will be described in more detail with reference to FIG. 6.

The second and third body portions 152, 153 extend from side surfaces of the base 110 to the first body portion 151. In an exemplary embodiment, the second and third body portions 152, 153 may include sliding grooves for receiving the first filter FT1. The first filter FT1 is received in the sliding grooves.

The first to third body portions 151 to 153 and the cover 120 surround the first filter FT1. In addition, the first to third body portions 151 to 153 block air.

Thus, air suctioned by the suction fan 140 mainly (substantially) passes through the first filter FT1 and is discharged through the first discharge port 112.

The second securing member 161 is disposed between the first securing member 150 and the suction fan 140. The second securing member 161 secures the first light emitting module 162 such that a first light emitting diode 163 included in the first light emitting module 162 faces one surface of the first filter FT1. The second securing member 161 may include a plurality of poles not to obstruct the flow of air while securing the first light emitting module 162 as shown in FIG. 1. This will be described in more detail with reference to FIG. 2.

The first light emitting module 162 may include at least one first light emitting diode 163 and a printed circuit board for mounting the first light emitting diode 163 thereon. The printed circuit board provides an interface between the controller 190 and the first light emitting diode 163. The first light emitting module 162 operates in response to control by the controller 190. The first light emitting diode 163 may emit light such as UV light toward the one surface of the first filter FT1.

The first filter FT1 may include a photocatalyst providing a deodorization function when exposed to light, such as UV light. Thus, in an operation mode, the first light emitting diode 163 emits UV light to the first filter FT1 to remove harmful substances from air suctioned by the suction fan 140 while harmful substances pass through the first filter FT1.

The third securing member 170 and the fourth securing member 181 are provided to form a symmetrical structure about the suction fan 140 with respect to the first securing member 150 and the second securing member 161. That is, the third securing member 170 and the fourth securing member 181 are disposed between the suction fan 140 and the second discharge port 113 to be similar to the first securing member 150 and the second securing member 161, respectively.

The third securing member 170 is disposed between the suction fan 140 and the second discharge port 113. The third securing member 170 supports the second filter FT2 such that one surface of the second filter FT2 faces the suction fan 140 in an X− direction intersecting the Z+ direction. Like the first securing member 150, the third securing member 170 includes body portions. The body portions of the third securing member 170 and the cover 120 surround the second filter FT2. Accordingly, air suctioned by the suction fan 140 mainly (substantially) passes through the second filter FT2 and the passed air is discharged through the second discharge port 113.

The fourth securing member 181 is disposed between the third securing member 170 and the suction fan 140. The fourth securing member 181 includes a plurality of poles for securing the second light emitting module 182 such that a light emitting diode included in the second light emitting module 182 faces the one surface of the second filter FT2.

The second filter FT2 and the second light emitting module 182 have similar shapes to the first filter FT1 and the first light emitting module 162, respectively.

According to these structures, in an operation mode, the second light emitting module 182 may emit UV light to the second filter FT2 to remove harmful substances from air suctioned by the suction fan 140 while the harmful substances pass through the second filter FT2.

According to an exemplary embodiment, the suction fan 140 is disposed to suction air in the Z+ direction. With this structure, the deodorizing device 100 has a reduced thickness. In addition, air suctioned through the suction port is discharged through two discharge ports 112, 113. Accordingly, the deodorizing device 100 capable of deodorizing a large amount of air per hour and having a reduced thickness is provided.

The controller 190 controls the overall operation of the deodorizing device 100. The controller 190 may be disposed in a suitable region so as not to obstruct the flow of air in the interior space of the housing 130. The controller 190 may control the suction fan 140 and the first and second light emitting modules 162, 182 in response to control signals from outside thereof.

In an exemplary embodiment, the deodorizing device 100 may further include visible light emitting diodes 195. The visible light emitting diodes 195 operate in response to control by the controller 190. The visible light emitting diodes 195 may emit visible light in a Z− direction. In this embodiment, portions of the base 110, which overlap the visible light emitting diodes 195, may be formed of transparent materials.

It will be understood that the timing of operating the visible light emitting diodes 195 may be changed in various ways. For example, when the suction fan 140 and the first and second light emitting modules 162, 182 are operated (that is, in an operation mode), the controller 190 may stop light emission from the visible light emitting diodes 195. The controller 190 may control the visible light emitting diodes 195 to emit light when operation of the suction fan 140 and the first and second light emitting modules 162, 182 is stopped. In an exemplary embodiment, the controller 190 may operate the visible light emitting diodes 195 in response to a control signal from outside thereof.

In FIG. 1, two discharge ports, and the filters FT1, FT2, the light emitting modules 162, 182 and the securing members 150, 161, 170, 181, which correspond to the two discharge ports, are illustrated. However, it should be understood that inventive concepts are not limited thereto. For example, the deodorizing device 100 may include one discharge port or three or more discharge ports. In this case, the deodorizing device 100 may include filters, light emitting modules, and securing members for supporting the filters and the light emitting modules, in correspondence with one or more discharge ports, respectively.

Figure 2:
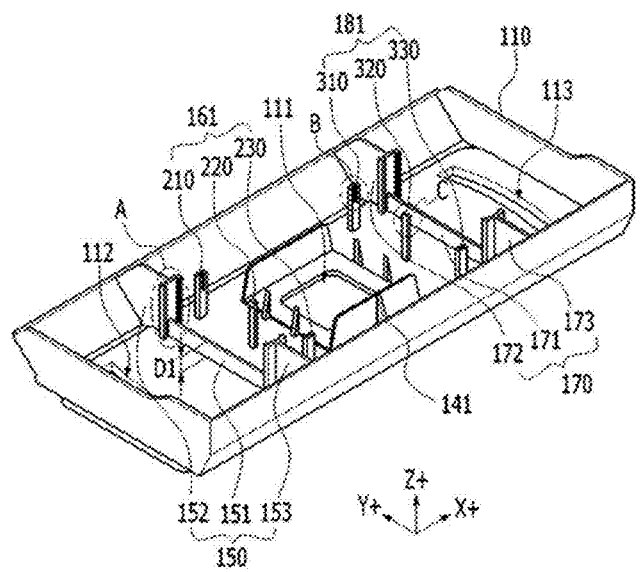
FIG. 2 is a perspective view of a base and first to fourth securing members of FIG. 1.
Figure 3:
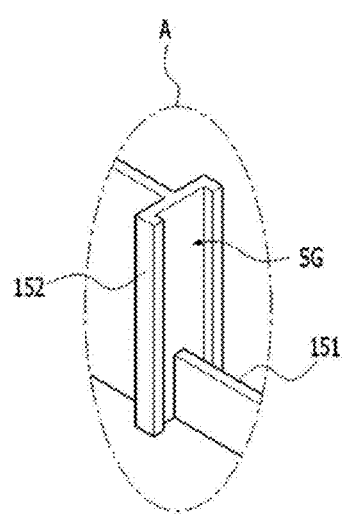
FIG. 3 is an enlarged view of Region A of FIG. 2.
Figure 4:
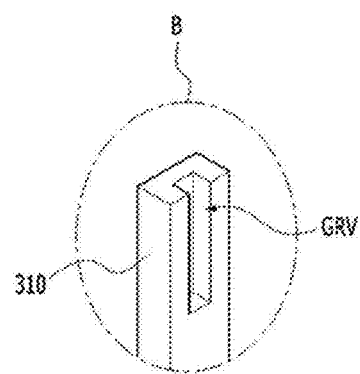
FIG. 4 is an enlarged view of Region B of FIG. 2.
Figure 5:
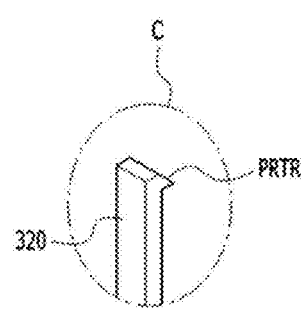
FIG. 5 is an enlarged view of Region C of FIG. 2.

FIG. 2 is a perspective view of the base 110 and the first to fourth securing members 150, 161, 170, 181 of FIG. 1. FIG. 3 is an enlarged view of Region A of FIG. 2. FIG. 4 is an enlarged view of Region B of FIG. 2. FIG. 5 is an enlarged view of Region C of FIG. 2.

Referring to FIG. 2, the suction port 111 is formed in a central region of the base 110 and disposed between the first and second discharge ports 112, 113.

The first securing member 150 includes the first to third body portions 151 to 153 for supporting the first filter FT1. The first body portion 151 is disposed between the second and third body portions 152, 153 and separates the first filter FT1 (see FIG. 1) from the bottom surface of the base 110 by a certain distance D1. The second and third body portions 152, 153 support the first filter FT1 together with the first body portion 151. Referring to FIG. 3, each of the second and third body portions 152, 153 includes a sliding groove SG for receiving the first filter FT1. The sliding groove SG is provided to the second and third body portions, whereby a user can easily secure the first filter FT1 to the first securing member 150 and the first filter FT1 can be firmly secured to the first securing member 150.

Referring again to FIG. 2, the third securing member 170 includes fourth to sixth body portions 171 to 173 for supporting the second filter FT2 (see FIG. 1). The fourth to sixth body portions 171 to 173 may have similar shapes to the first to third body portions 151 to 153, respectively.

The second securing member 161 includes first to third poles 210 to 230 for securing the first light emitting module 162 (see FIG. 1). The first to third poles 210 to 230 are disposed between the suction port 111 and the first securing member 150. The first to third poles 210 to 230 may be configured like fourth to sixth poles 310 to 330 of the fourth securing member 181, respectively. Next, the fourth securing member 181 will be described.

The fourth securing member 181 includes the fourth to sixth poles 310 to 330 for securing the second light emitting module 182. The fourth to sixth poles 310 to 330 are disposed between the suction port 111 and the third securing member 170. Referring to FIG. 4, each of the fourth and sixth poles 310, 330 may include a groove GRV receiving the second light emitting module 182 (see FIG. 1). Thus, the second light emitting module 182 is secured by the fourth and sixth poles 310, 330. The fifth pole 320 is disposed between the fourth and sixth poles 310, 330 and further secures the second light emitting module 182. Referring to FIG. 5, the fifth pole 320 includes a protrusion PRTR extending in the X+ direction in an upper portion thereof. The protrusion PRTR may allow the second light emitting module 182 secured to the fourth and sixth poles 310, 330 not to deviate, for example, in the Z+ direction. That is, the second light emitting module 182 is firmly secured by the fifth pole 320.

For example, the second light emitting module 182 may be prevented from suffering from unintended shaking due to air circulated in the housing 130 (see FIG. 1).

Figure 6:
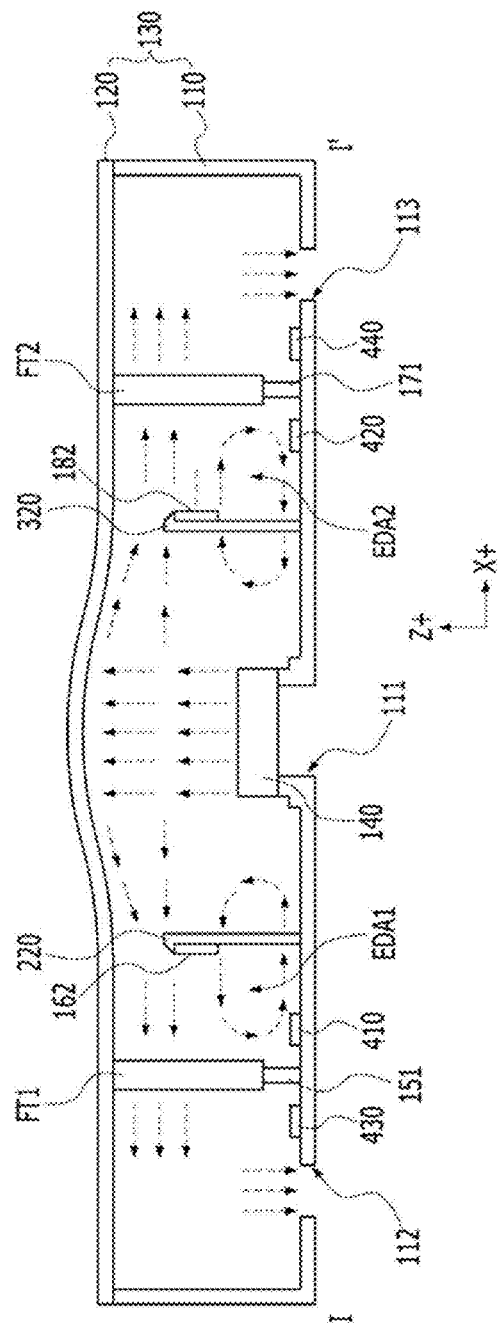
FIG. 6 is a sectional view of the deodorizing device taken along Line I-I' of FIG.

FIG. 6 is a sectional view of the deodorizing device 100 taken along Line I-I' of FIG. 1.

Referring to FIG. 6, the suction fan 140 suctions air in the Z+ direction through the suction port 111. In FIG. 6, air is indicated by dashed lines. Air impinges against the cover 120 and then flows in the X− and X+ directions. Air flowing in the X− direction passes through the first filter FT1, and the passed air is discharged through the first discharge port 112. Air flowing in the X+ direction passes through the second filter FT2 and the passed air is discharged through the second discharge port 113.

The suction fan 140 is placed to suction air in the Z+ direction, thereby reducing the thickness of the deodorizing device 100. In addition, air is discharged through two discharge ports 112, 113, whereby the deodorizing device 100 may efficiently suction and discharge air even though the X− and X+ directions, in which air passes through the filters FT1, FT2, intersect the Z+ direction, in which air is suctioned. Therefore, the deodorizing device 100 according to the exemplary embodiment can deodorize a large amount of air while having a reduced thickness.

The first filter FT1 is spaced apart from the bottom surface of the base 110 by the body portion 151 and the second filter FT2 is spaced apart from the bottom surface of the base 110 by the body portion 171. In addition, the first filter FT1 and the second filter FT2 adjoin the cover 120. Since air is suctioned in the Z+ direction to reach the cover 120 and move in the X− and X+ directions, considering that air mainly flows along an upper portion of the housing 130, the filters FT1, FT2 spaced apart from the bottom surface of the base 110 and contacting the cover 120 are placed in a main flow path of air, whereby these positions of the filters FT1, FT2 allow air to effectively pass through the filters FT1, FT2.

In addition, since the first filter FT1 is surrounded by the body portions 151 to 153 and the cover 120 and the second filter FT2 is surrounded by the body portions 171 to 173 and the cover 120, most air flowing in the X− and X+ directions passes through the first and second filters FT1, FT2 and then is discharged through the discharge ports 112, 113, thereby minimizing the amount of air discharged without passing through the first and second filters FT1, FT2. Accordingly, the deodorizing device 100 may have improved deodorizing efficiency. In addition, the filters FT1, FT2 have sizes reduced by areas corresponding to the body portions 151, 171 thereof, thereby reducing manufacturing costs of the filters FT1, FT2.

Further, the first light emitting module 162 is disposed between the first filter FT1 and the suction fan 140 and emits light to the first filter FT1, and the second light emitting module 182 is disposed between the second filter FT2 and the suction fan 140 and emits light to the second filter FT2. Further, the first body portion 151 supports the first filter FT1 and blocks air. Due to the first body portion 151, eddy air EDA1, for example, turbulence, may be generated in a region adjacent to the first body portion 151. The fourth body portion 171 supports the second filter FT2 and blocks air. Due to the fourth body portion 171, eddy air EDA2 may be generated in a region adjacent to the fourth body portion 171. Generation of the eddy air EDA1, EDA2 may increase a time period for which air stays between each filter and the corresponding light emitting module. Since a surface of a filter exposed to light from a light emitting module provides more effective deodorization, harmful substances in air can be efficiently removed by the surface of the filter exposed to the light from the light emitting module with increasing time period for which the air stays between the filter and the light emitting module. Accordingly, the deodorizing device 100 according to the exemplary embodiment may have improved deodorizing efficiency.

In addition, since each light emitting module is disposed between the corresponding filter and the suction fan 140, air cooling of each light emitting module may be further provided due to the eddy air EDA1, EDA2.

In an exemplary embodiment, the deodorizing device 100 includes first and second photosensors 410, 420. The first photosensor 410 senses intensity of light, for example, the intensity of UV light, emitted from the first light emitting module 162. The second photosensor 420 senses the intensity of light emitted from the second light emitting module 182. Each of the first and second photosensors 410, 420 may be disposed in a suitable region so as not to obstruct the flow of air. When the sensed intensity of light is lower than a threshold value, the controller 190 may generate an alarm signal. Information indicating that the light emitting modules 162, 182 need to be replaced may be provided to a user based on the alarm signal.

In an exemplary embodiment, the deodorizing device 100 further includes first and second air sensors 430, 440. Each of the first and second air sensors 430, 440 is configured to sense an amount (or concentration) of one of various gases, for example, ammonia gas, hydrogen sulfide gas, trimethylamine gas, methyl mercaptan gas, and ethylene gas, which are included in air. The controller 190 may operate the suction fan 140 (see FIG. 1) and the light emitting modules 162, 182 according to a control signal from outside thereof and sensing results of the first and second air sensors 430, 440.

Figure 7:
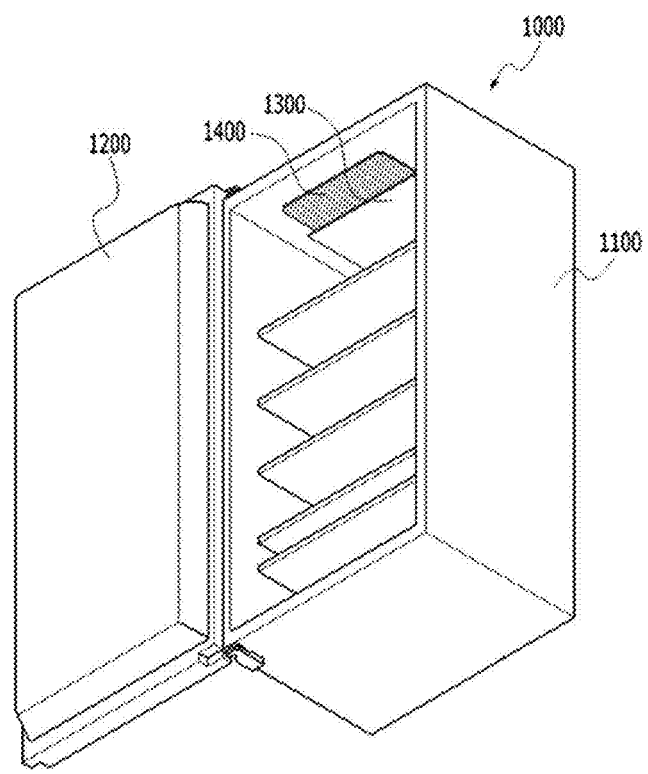
FIG. 7 is a perspective view of a refrigerator according to an exemplary embodiment of the present invention.

FIG. 7 is a perspective view of a refrigerator 1000 according to an exemplary embodiment of the present invention.

Referring to FIG. 7, the refrigerator 1000 includes a main body 1100, a door 1200, a main controller 1300, and a deodorizing device 1400.

The main body 1100 and the door 1200 define an internal space of the refrigerator 1000.

The door 1200 is secured to the refrigerator 1000 by a component, such as a hinge, and is openable and closable.

The main controller 1300 is disposed on an upper plate of the main body 1100. The main controller 1300 controls overall operations of the refrigerator 1000. The deodorizing device 1400 is further disposed on the upper plate of the main body 1100. The deodorizing device 1400 may have a similar shape to the deodorizing device 100 described with reference to FIG. 1 and may be operated in response to a control signal from the main controller 1300.

It will be understood that the refrigerator 1000 may include various components in addition to those set forth above. For example, the refrigerator 1000 may further include a display device and the main controller 1300 may display various pieces of information through the display device.

In an exemplary embodiment, the controller 190 of the deodorizing device 1400 and the main controller 1300 may be provided as separate components. However, it should be understood that the inventive concepts are not limited thereto. For example, the controller 190 may be provided as a component included in the main controller 1300. In this example, the main controller 1300 may be configured to perform a function of the controller 190.

Although FIG. 7 illustrates that the main controller 1300 and the deodorizing device 1400 are disposed on the upper plate of the main body 1100, it should be understood that the inventive concepts are not limited thereto. Regions in which the main controller 1300 and the deodorizing device 1400 are placed may be changed in various ways.

Figure 8:
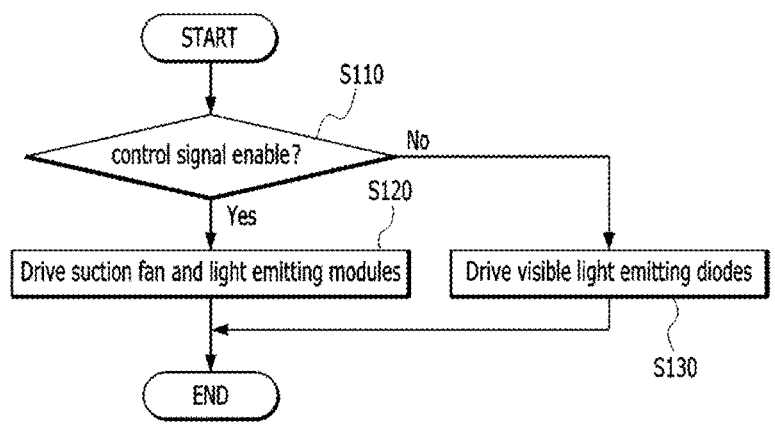
FIG. 8 is a flowchart illustrating a method of operating a deodorizing device mounted in a refrigerator.

FIG. 8 is a flowchart illustrating a method of operating the deodorizing device 1400 mounted in the refrigerator 1000.

Referring to FIGS. 7 and 8, depending upon whether a control signal provided from the main controller 1300 of the refrigerator 1000 is enabled in step S110, step S120 or S130 is performed.

In step S120, the suction fan 140 (see FIG. 1) and the light emitting modules 162, 182 (see FIG. 1) are operated. The controller 190 (see FIG. 1) of the deodorizing device 1400 may operate the suction fan 140 and the light emitting modules 162, 182 when the control signal is enabled. For example, the main controller 1300 may enable the control signal when the door 1200 is closed and may disable the control signal when the door 1200 is open. In this case, a user may be protected from being exposed to UV light emitted from the light emitting modules 162, 182. For example, the main controller 1300 may periodically enable the control signal at predetermined time intervals when the door 1200 is closed. In addition, the main controller 1300 may enable the control signal at a suitable timing.

In step S130, the visible light emitting diodes 195 (see FIG. 1) are operated. The controller 190 operates the visible light emitting diodes 195 when the control signal is disabled. In the case where the control signal is disabled when the door 1200 is open, the deodorizing device 1400 may provide a visual effect of emitting visible light when the door 1200 is open.

Figure 9:
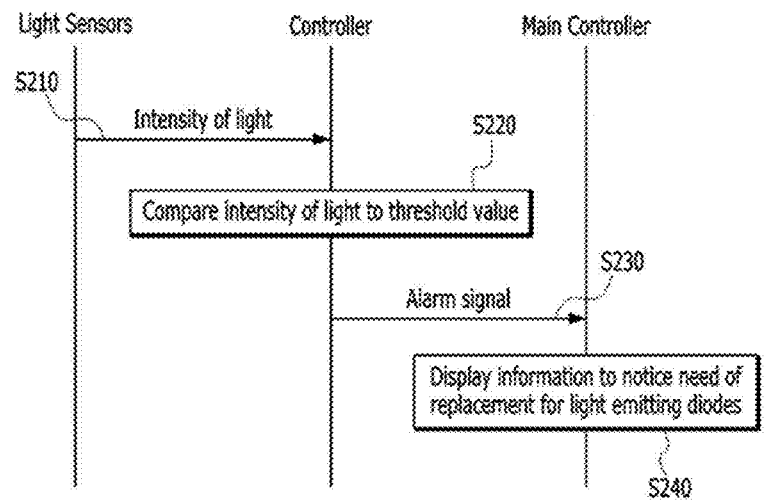
FIG. 9 is a diagram illustrating a method of operating a refrigerator, according to an exemplary embodiment of the present invention.

FIG. 9 is a diagram illustrating a method of operating the refrigerator 1000, according to an exemplary embodiment of the present invention.

Referring to FIGS. 7 and 9, in step S210, the photosensors 410, 420 (see FIG. 6) of the deodorizing device 1400 provide information about the intensity of light to the controller 190 (see FIG. 1) of the deodorizing device 1400.

In step S220, the controller 190 compares the intensity of light with a threshold value. The case where the intensity of light is lower than the threshold value may mean that remaining lifespan of the light emitting diodes in the light emitting modules 162, 182 is relatively short. The case where the intensity of light is higher than or equal to the threshold value may mean that remaining lifespan of the light emitting diodes in the light emitting modules 162, 182 is relatively long. In step S230, when the intensity of light is lower than the threshold value, the controller 190 transmits an alarm signal to the main controller 1300.

In step S240, the main controller 1300 may display requirement for replacement of the light emitting modules 162, 182 or the light emitting diodes on the display device of the refrigerator 1000.

Figure 10:
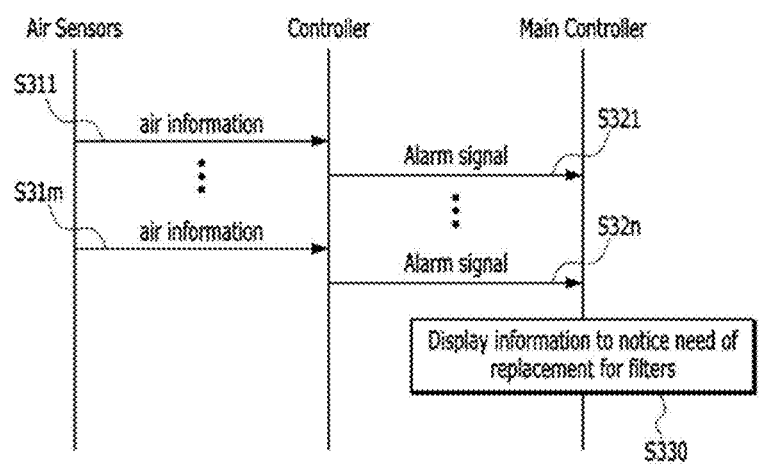
FIG. 10 is a diagram illustrating a method of operating a refrigerator, according to another exemplary embodiment of the present invention.

FIG. 10 is a diagram illustrating a method of operating the refrigerator 1000, according to another exemplary embodiment of the present invention.

Referring to FIGS. 7 and 10, in steps S311 to S31$m$, the air sensors 430, 440 (see FIG. 6) of the deodorizing device 1400 sense air and provide information indicating a state of the air to the controller 190 (see FIG. 1) of the deodorizing device 1400. In steps S321 to S32$n$, the controller 190 transmits alarm signals to the main controller 1300 in response to the information received from the air sensors 430, 440. For example, when the amount of materials in air sensed in each of steps S321 to S32$n$ is higher than a threshold value, an alarm signal may be generated.

In step S330, the main controller 1300 may display requirement for replacement of the filters FT1, FT2 on the display device based on the received alarm signals. For example, when the alarm signals continue to be received even though the suction fan 140 and the light emitting modules 162, 182 are being operated, the main controller 1300 may announce that the filters FT1, FT2 need to be replaced.

Figure 11:
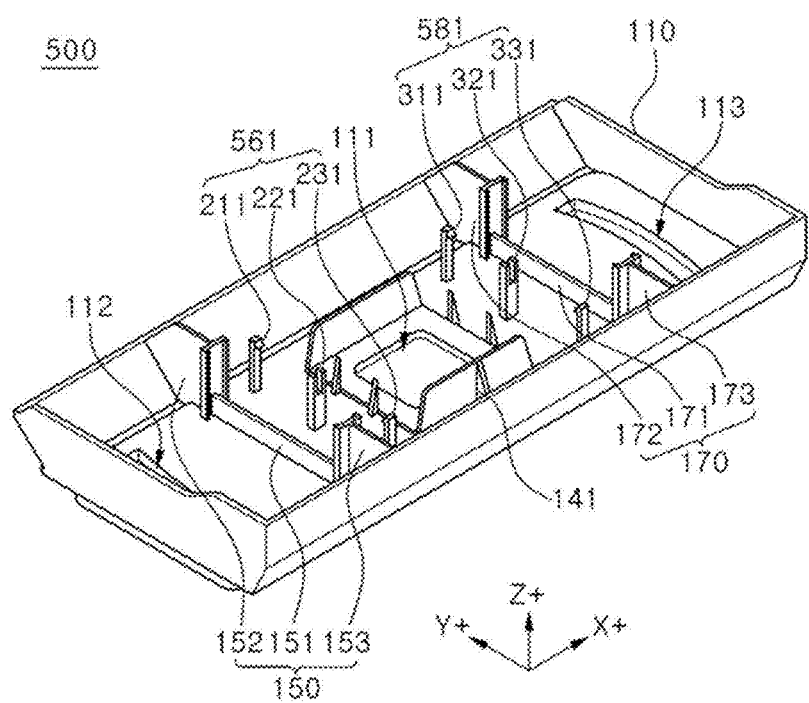
FIG. 11 is an exemplary diagram of a deodorizing device according to another exemplary embodiment of the present invention.
Figure 12:
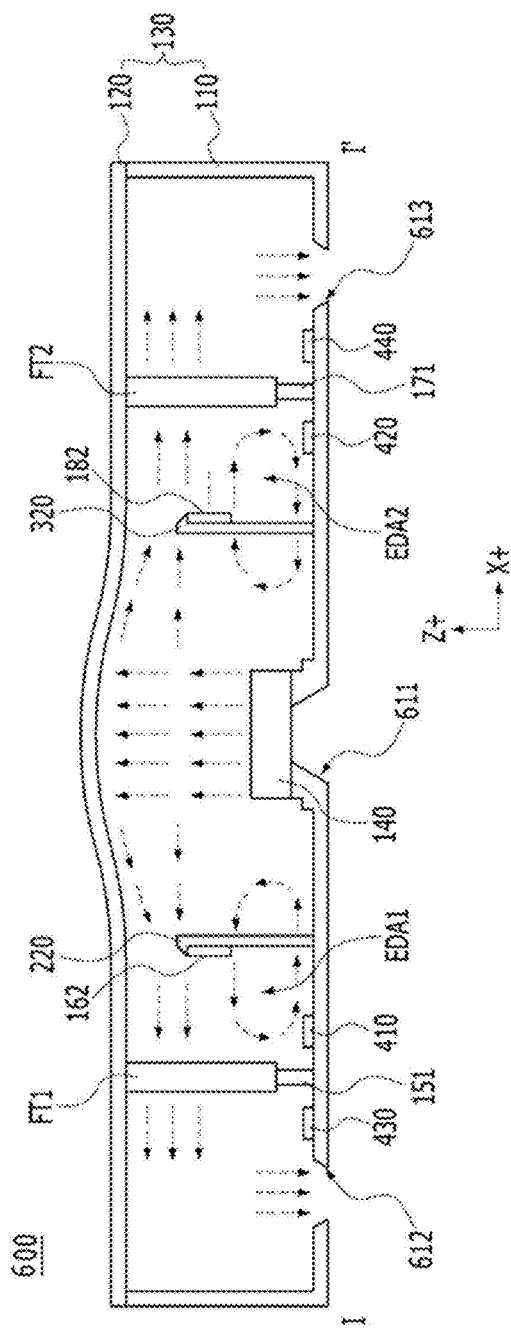
FIG. 12 is an exemplary diagram of a deodorizing device according to a further exemplary embodiment of the present invention.
Figure 13:
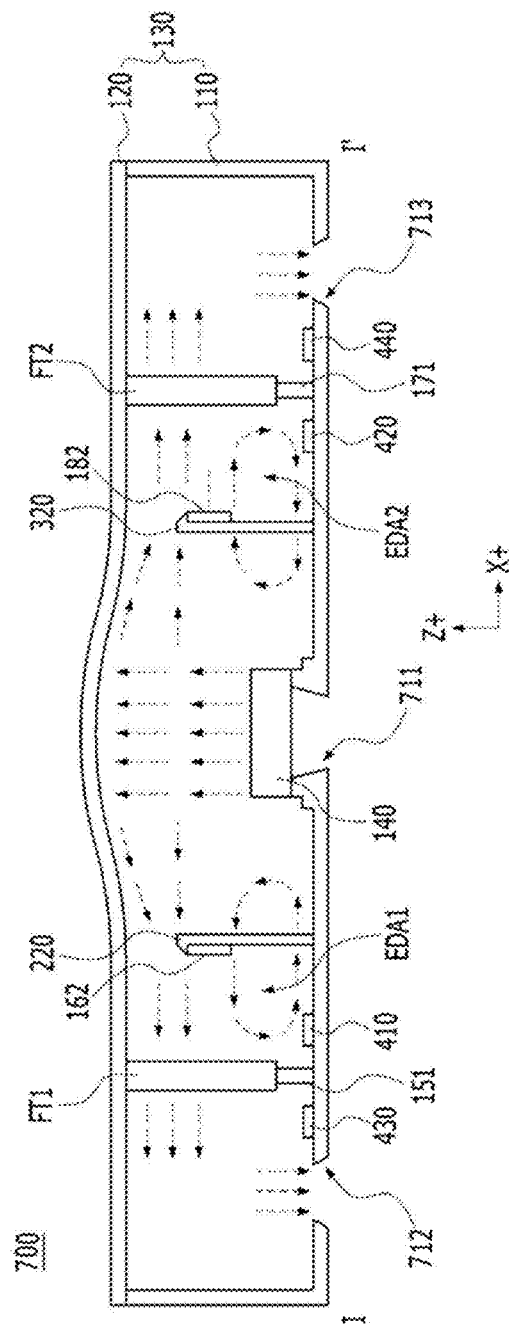
FIG. 13 is an exemplary diagram of a deodorizing device according to yet another exemplary embodiment of the present invention.

FIGS. 11 to 13 illustrate other exemplary embodiments of deodorizing devices. In description of the deodorizing devices according to the other exemplary embodiments with reference to FIGS. 11 to 13, descriptions of the same components as the deodorizing device 100 of the above embodiments will be omitted and the following description will focus on different features. For the omitted description, refer to the description of the deodorizing device 100 according to the above embodiments.

FIG. 11 is an exemplary diagram of a deodorizing device according to another exemplary embodiment of the present invention.

Referring to FIG. 11, in a deodorizing device 500 according to another exemplary embodiment, a second securing member 561 and a fourth securing member 581 have different structures from those of the above embodiment, respectively. The second securing member 561 includes a first pole 211, a second pole 221, and a third pole 231. Each of the first pole 211 and the third pole 231 has a structure in which an upper portion thereof protrudes in a lateral direction. The first pole 211 and the third pole 231 are disposed near side surfaces of the base 110, respectively. In addition, the first pole 211 and the third pole 231 are arranged such that the protruding upper portions thereof face each other.

The second pole 221 is disposed between the first pole 211 and the third pole 231. The second pole 221 has an upper portion penetrated from a side surface thereof facing the first pole 211 to a side surface thereof facing the third pole 231. The penetrated portion of the second pole 221 extends up to an upper surface of the second pole 221.

When the first light emitting module 162 (see FIG. 1) is secured to the second securing member 561, the first light emitting module 162 is inserted into the second pole 221 from the upper surface of the second pole 221 in a downward direction. Here, the protruding upper portions of the first pole 211 and the third pole 231 contact both ends of an upward-facing side surface of the first light emitting module 162, respectively. Thus, the first light emitting module 162 is spaced apart from the bottom surface of the base 110 by a certain distance due to the second pole 221, and when the deodorizing device 500 is shaken, the first pole 211 and the third pole 231 may prevent the first light emitting module 162 from deviating from the second pole 221.

In addition, since the first pole 211 and the third pole 231 are arranged to face each other, both side surfaces of the first light emitting module 162, which face side surfaces of the base 110, contact side surfaces of the first pole 211 and the third pole 231, respectively, when the first light emitting module 162 is mounted on the second securing member 561. Thus, when the deodorizing device 500 is shaken, the first light emitting module 162 is secured by the first pole 211 and the third pole 231 so as not to be moved in a direction from side to side thereof.

A fourth pole 311, a fifth pole 321, and a sixth pole 331 of the fourth securing member 581 correspond to the first pole 211, the second pole 221, and the third pole 231 of the second securing member 561, respectively.

FIG. 12 is an exemplary diagram of a deodorizing device according to a further exemplary embodiment of the present invention.

Referring to FIG. 12, discharge ports 612, 613 have structures in which cross-sectional areas thereof gradually decrease from the interior of the housing 130 toward the exterior of the housing 130.

Since the discharge ports 612, 613 have gradually narrowing structures, air pressure gradually increases when air passes through the discharge ports 612, 613.

Inner walls of the base 110, which form the discharge ports 612, 613, have slopes such that a distance between the inner walls facing each other gradually decreases from the interior of the housing 130 toward the exterior of the housing 130. Thus, when air passes through the discharge ports 612, 613, a portion of the air collides against the inner walls of the base 110, which have the discharge ports 612, 613 therein. In addition, an eddy is generated due to the air colliding against the inner walls of the base 110. Such an eddy obstructs the flow of air discharged out of the housing 130.

As such, due to an eddy and increase in air pressure caused by the discharge ports 612, 613 having gradually narrowing structures, the amount of air discharged from the interior of the housing 130 toward the exterior thereof is less than the amount of air suctioned into the housing 130. Thus, a moving rate of air inside the housing 130 decreases. As a result, a time period for which air remains inside the housing 130 is increased. Air is deodorized for a longer time period with increasing time period for which air remains inside the housing 130.

Accordingly, the deodorizing device 600 according to this embodiment may deodorize air for a long period of time due to the structures of the discharge ports 612, 613 and have improved deodorizing performance.

In addition, a suction port 611 may have a structure in which a cross-sectional area thereof gradually decreases from the exterior of the housing 130 toward the interior thereof. Air passing through the suction port 611 is suctioned into the housing 130 by the fan 140 at high rate. Here, the structure of the suction port 611, which gradually decreases in an air flow direction, efficiently guides air outside the housing 130 toward the fan 140. Thus, the air suctioning rate into the housing 130 is improved due to the suction port 611 having a gradually narrowing structure and the fan 140.

That is, the deodorizing device 600 according to this embodiment may suction a larger amount of air through the suction port 611 than the amount of air discharged through the discharge ports 612, 613. Therefore, the time period for which air remains in the housing 130 is further increased, whereby air inside the housing 130 can be deodorized much longer.

The structure wherein both the discharge ports 612, 613 and the suction port 611 have a gradually narrowing structure in the air flow direction may provide better deodorizing performance to the deodorizing device 600 than the structure wherein only the discharge ports 612, 613 have a gradually narrowing structure.

As in this exemplary embodiment, the deodorizing device 600 capable of deodorizing air for a long period of time may be applied to a small space, a space requiring a low air circulation strength, or a place in which air needs to be prevented from getting dry due to air circulation.

FIG. 13 is an exemplary diagram of a deodorizing device according to yet another exemplary embodiment of the present invention.

Referring to FIG. 13, a suction port 711 and discharge ports 712, 713 have structures in which sizes thereof gradually increase in the air flow direction.

The suction port 711 has a structure in which a cross-sectional area thereof gradually increases from the exterior of the housing 130 toward the interior thereof. Thus, the inner walls of the base 110, which have the suction port 711 therein, have slopes such that a distance between the inner walls facing each other increases from the exterior of the housing 130 toward the interior thereof.

Due to the suction port 711 having the structure set forth above, when air is suctioned into the housing 130, a flow path of air gradually increases in size. Thus, since air pressure decreases as air passes through the suction port 711, loss of air decreases during suctioning. That is, air outside the housing 130 may be suctioned into the housing 130 through the fan 140 without loss at the suction port 711.

The discharge ports 712, 713 have structures in which cross-sectional areas thereof gradually increase from the interior of the housing 130 toward the exterior thereof. Thus, the inner walls of the base 110, which have the discharge ports 712, 713 therein, have slopes such that a distance between the inner walls facing each other increases from the interior of the housing 130 toward the exterior thereof. Therefore, the discharge ports 712, 713 have structures in which the cross-sectional areas thereof increase from the interior of the housing 130 toward the exterior thereof.

Due to the discharge ports 712, 713 having the structures set forth above, when deodorized air is discharged from the housing 130, a flow path of air gradually increases in size. Thus, since the air pressure decreases as air passes through the discharge ports 712, 713, deodorized air may be discharged from the housing 130 without loss.

In addition, according to this exemplary embodiment, due to the structures of the discharge ports 712, 713, an eddy due to collision of air against the inner walls of the base 110 after passing through the discharge ports 712, 713 can be prevented. Further, the base 110 includes two discharge ports 712, 713. That is, a space through which air is discharged from the housing 130 is larger than a space through which air is suctioned into the housing 130. That is, in the deodorizing device 700 of this exemplary embodiment, suctioned air flows inside the housing 130 at high rate to be deodorized and is then discharged from the housing 130. Therefore, the deodorizing device 700 according to this exemplary embodiment can achieve deodorization of air at high rate through fast air circulation inside the housing 130.

The deodorizing device 700 using fast air circulation may be applied to a large space, such as a refrigeration device, to achieve efficient deodorization of the large space.

Although the present invention has been described with reference to some embodiments in conjunction with the accompanying drawings, it should be understood that the foregoing embodiments are provided merely for aiding in overall understanding of the present invention and are not to be construed in any way as limiting the present invention, and that various modifications, variations and alterations can be made by those skilled in the art without departing from the spirit and scope of the present invention.

Therefore, the scope of the disclosure should not be limited to the foregoing exemplary embodiments and should be interpreted according to the following appended claims as covering all modifications or variations derived from the appended claims and equivalents thereof.

What is claimed is:

1. A deodorizing device comprising:
    a base, in which a suction port and a discharge port are disposed;
    a cover coupled to the base;
    a suction fan secured to the base and suctioning air through the suction port;
    a first securing member disposed between the suction port and the discharge port and supporting a filter;
    a light emitting module comprising a light emitting diode; and
    a second securing member supporting the light emitting module,
    wherein:
    the first securing member comprises a first body portion separating the filter from the base; and
    the suction fan suctions the air in a first direction through the suction port and the first securing member supports the filter such that a surface of the filter, through which the air passes, faces in a second direction perpendicular to the first direction.

2. The deodorizing device according to claim 1, wherein:
    the first securing member further comprises second and third body portions comprising sliding grooves for receiving the filter;
    the first body portion is disposed between the second and third body portions;
    the first to third body portions surround the filter; and
    the first to third body portions block the air.

3. The deodorizing device according to claim 1, wherein the second securing member comprises:
    first and second poles comprising grooves for securing the light emitting module; and
    a third pole disposed between the first and second poles and having a protrusion for further securing one side of the light emitting module,
    wherein the second securing member is disposed between the suction port and the first securing member.

4. The deodorizing device according to claim 1, wherein an inner wall of the base has a slope, the inner wall forming the suction port.

5. The deodorizing device according to claim 4, wherein the suction port has a cross-sectional area increasing from an exterior of the base toward an interior of the base.

6. The deodorizing device according to claim 1, wherein an inner wall of the base has a slope, the inner wall forming the discharge port.

7. The deodorizing device according to claim 6, wherein the discharge port has a cross-sectional area increasing from an interior of the base toward an exterior of the base.

8. A deodorizing device comprising:
    a base, in which a suction port and a discharge port are disposed;
    a suction fan secured to the base and suctioning air through the suction port;
    a filter disposed between the suction port and the discharge port; and
    a light emitting module disposed between the suction port and the filter, the light emitting module comprising a substrate and a light emitting diode placed on one surface of the substrate;
    wherein:
    the one surface of the substrate faces the filter and an opposing surface of the substrate faces air suctioned through the suction port; and
    the suction fan suctions the air in a first direction through the suction port and the first securing member supports the filter such that a surface of the filter, through which the air passes, faces in a second direction perpendicular to the first direction.

9. The deodorizing device according to claim 8, further comprising a first securing member supporting the filter.

10. The deodorizing device according to claim 9, wherein:
    the first securing member further comprises second and third body portions comprising sliding grooves for receiving the filter;
    a first body portion is disposed between the second and third body portions;
    the first to third body portions and a portion of the cover surround the first filter; and
    the first to third body portions block the air.

11. The deodorizing device according to claim 10, further comprising a second securing member supporting the light emitting module.

12. The deodorizing device according to claim 11, wherein the second securing member comprises:
    first and second poles comprising grooves for securing the light emitting module; and
    a third pole disposed between the first and second poles and having a protrusion for further securing one side of the light emitting module,
    wherein the second securing member is disposed between the suction port and the first securing member.

13. The deodorizing device according to claim 8, wherein an inner wall of the base has a slope, the inner wall forming the suction port.

14. The deodorizing device according to claim 13, wherein the suction port has a cross-sectional area increasing from an exterior of the base toward an interior of the base.

15. The deodorizing device according to claim 8, wherein an inner wall of the base has a slope, the inner wall forming the discharge port.

16. The deodorizing device according to claim 15, wherein the discharge port has a cross-sectional area increasing from an interior of the base toward an exterior of the base.

17. A refrigerator comprising:
    a main body;
    a door secured to the main body to open and close the main body;
    a deodorizing device secured inside the main body;
    a display device; and
    a main controller controlling the deodorizing device,
    wherein:
    the deodorizing device comprises:
    a base, in which a suction port and a discharge port are disposed;
    a cover coupled to the base;

a suction fan secured to the base and suctioning air through the suction port;

a first securing member disposed between the suction port and the discharge port and supporting a filter, the first securing member comprising a body portion separating the filter from the base;

a light emitting module comprising a light emitting diode;

a second securing member supporting the light emitting module;

a controller controlling the suction fan and the light emitting module; and an air sensor sensing air passing through the filter;

the controller generates alarm signals according to sensing results of the air sensor; and the main controller displays requirement for replacement of the light emitting diode on the display device based on the alarm signals.

18. The refrigerator according to claim 17, wherein the main controller enables a control signal when the door is closed, and the controller operates the suction fan and the light emitting module when the control signal is enabled.

19. The refrigerator according to claim 18, wherein the deodorizing device comprises visible light emitting diodes which are arranged on the base and operate in response to control by the controller, and the controller operates the visible light emitting diodes when the control signal is disabled.

20. The refrigerator according to claim 17, wherein:

the deodorizing device further comprises a photosensor sensing intensity of light emitted from the light emitting diode;

the controller generates an alarm signal when the sensed intensity of light is lower than a threshold value; and the main controller displays requirement for replacement of the light emitting diode on the display device in response to the alarm signal.

* * * * *